United States Patent [19] [11] 4,218,438
Callender et al. [45] Aug. 19, 1980

[54] ANTICOCCIDIAL COMBINATIONS COMPRISING NICARBAZIN AND THE POLYETHER ANTIBIOTICS

[75] Inventors: Maurice E. Callender, Indianapolis; Thomas K. Jeffers, Greenfield, both of Ind.

[73] Assignee: Eli Lilly and Company, Indianapolis, Ind.

[21] Appl. No.: 12,165

[22] Filed: Feb. 14, 1979

[51] Int. Cl.$^2$ .................. A61K 35/66; A61K 31/505; A61K 31/35
[52] U.S. Cl. .................................. 424/115; 424/181; 424/251; 424/283
[58] Field of Search .................. 424/115, 283, 251, 181

[56] References Cited
U.S. PATENT DOCUMENTS

| | | | |
|---|---|---|---|
| 3,761,594 | 9/1973 | Challey | 424/258 |
| 4,061,755 | 12/1977 | McDougald | 424/263 |
| 4,075,323 | 2/1978 | McDougald | 424/114 |
| 4,083,962 | 4/1978 | McDougald | 424/114 |
| 4,130,661 | 12/1978 | Kulsa et al. | 424/324 |

FOREIGN PATENT DOCUMENTS 1339467 12/1973 United Kingdom .
1463519 2/1977 United Kingdom .

OTHER PUBLICATIONS

Mitrovic et al.–Chem. Abst., vol. 83, (1975), p. 141,784j.

Primary Examiner—Sam Rosen
Attorney, Agent, or Firm—Kathleen R. S. Page; Arthur R. Whale

[57] ABSTRACT

The present invention is directed to novel anticoccidial compositions and methods of employing the same to control coccidiosis in poultry. These compositions comprise a polyether antibiotic and a second component selected from nicarbazin and 4,4'-dinitrocarbanilide.

33 Claims, No Drawings

ANTICOCCIDIAL COMBINATIONS COMPRISING NICARBAZIN AND THE POLYETHER ANTIBIOTICS

BACKGROUND OF THE INVENTION

Nicarbazin and the polyether antibiotics are known anticoccidials. However, certain strains of Eimeria, the causative organism of coccidiosis, exhibit or develop over time a resistance to certain of the anticoccidials. See "Chemotherapy of Chicken Coccidiosis," *Advances in Pharmacology and Chemotherapy II*, 221-293 (1973). The combinations of the present invention unexpectedly exhibit activity against strains which have reduced sensitivity to each compound when used individually. Furthermore, when employed alone at its accepted dose, nicarbazin causes some growth inhibition. See German Pat. No. 2,154,049. Therefore, it is desirable to reduce the dose of nicarbazin, if this can be achieved without reducing anticoccidial efficacy. The present combinations are also advantageous in that they permit the use of lower levels of nicarbazin.

Combinations of anticoccidials have previously been disclosed. Representative combinations include the following. U.S. Pat. Nos. 4,075,323 and 4,083,962, describe combinations of two polyether antibiotic anticoccidials. U.S. Pat. No. 4,061,755, is directed to the combination of monensin and metichlorpindol.

U.S. Pat. No. 3,761,594 describes the combination of meticlorpindol with 4-hydroxyquinolines. Nicarbazin has been combined with certain quanidine compounds (German Pat. No. 2,154,049). U.K. No. 1,463,519 describes the combination of purines with inter alia, monensin and nicarbazin.

SUMMARY

The present invention is directed to a process for controlling coccidiosis in poultry which comprises orally administering to the poultry a feedstuff comprising a first component which is a polyether antibiotic and a second component which is selected from the group consisting of nicarbazin and 4,4'-dinitrocarbanilide, said components being present in the feedstuff in amounts which, in combination, are synergistic as to at least one coccidiosis-causing strain of Eimeria.

The present invention is also directed to the compositions to be employed in the foregoing methods.

DETAILED DESCRIPTION

All of the compounds to be employed in the present invention are known in the prior art.

Nicarbazin and 4,4'-dinitrocarbanilide are taught in U.S. Pat. No. 2,731,382. Nicarbazin is a complex of 4,4'-dinitrocarbanilide and 2-hydroxy-4,6-dimethylpyrimidine, but the 4,4'-dinitrocarbanilide alone exhibits anticoccidial activity. See Science 122, 244 (1955).

The polyether antibiotics are a class of antibiotics produced by the Streptomyces genus of microorganisms. They are characterized by comprising a multiplicity of cyclic ethers in their structures. The class is reviewed in Kirk-Othmer: *Encyclopedia of Chemical Technology*, Vol. 3, Third Edition (John Wiley & Sons, Ind., 1978), page 47 et seq.; in *Annual Reports in Medicinal Chemistry* Volume 10 (Academic Press, N.Y. 1975), page 246 et seq.; and in *J. Chrom. Lib.*, Vol. 15 (Elsevier Scientific Publishing Co., N.Y. 1978), page 488 et seq.

Like other products of fermentation origin, many of the polyether antibiotics comprise more than one factor. The various factors are all usable in the present invention. Further, many of these antibiotics readily form ethers, esters, salts, or other derivatives, which are either active as such or are converted in vivo to the basic antibiotic. Such derivatives can also be employed in the present invention. All that is necessary is that an active moiety of a polyether antibiotic be delivered in vivo.

Representative polyether antibiotics include the following: monensin (factors A, B, and C), laidlomycin, nigericin, grisorixin, dianemycin, lenoremycin, salinomycin, narasin, lonomycin, antibiotic X206, alborixin, septamycin, antibiotic 204A, etheromycin, lasalocid (factors A, B, C, D, and E), isolasalocid A, lysocellin, and antibiotic A23187.

Preferred polyether antibiotics include monensin, narasin, lasalocid, salinomycin, A-204, lonomycin, X-206, nigericin, and dianemycin, and especially monensin, narasin, lasalocid, and A-204.

The methods and compositions of the present invention can be used with all species of poultry. Because of their economic importance, chickens and turkeys are the principal species requiring anticoccidial treatment. However, the present invention can be practiced with other poultry, such as ducks, geese, pheasants, and quail.

The present invention is practiced in the usual manner of anticoccidials. Since coccidiosis affects the intestinal tract, the compositions of the present invention are those which are suited for oral administration. The polyether antibiotics are generally of low solubility in water, even in the sodium or other salt form. Therefore, the present invention is preferably practiced by administering the subject combinations in a feedstuff rather than in drinking water. Furthermore, it is the practice of the industry to supply poultry with only one source of feed, constituting the entire food supply of the poultry. Therefore, in a preferred practice of the present invention, the anticoccidial combinations are supplied in a total feed, with concentrations adjusted accordingly. Those skilled in the art, however, will recognize that concentrations are to be adjusted upward, should it be desired to supply poultry with multiple sources of food only one of which contains the combinations of the present invention.

The components of the present combinations are employed in amounts which, in combination, are synergistic as to at least one coccidiosis-causing organism. In general, the maxima to be employed in accordance with the present invention are the same as the maxima for anticoccidial treatment by the individual components. The lower limits in accordance with the present invention are generally less than for therapy by the individual components, especially where the components are being used to minimize side effects of either individual component. Accordingly, the present invention is generally practiced with compositions containing from about 20 to 125 ppm of nicarbazin or from about 25 to about 150 ppm of 4,4'-dinitrocarbanilide, and an amount of a polyether antibiotic which, in combination with the first component, is synergistic as to at least one coccidiosis-causing strain of Eimeria. Representative amounts of selected polyether antibiotics are as follows:

from about 20 to about 120 ppm of monensin;
from about 25 to about 100 ppm of narasin;
from about 35 to about 125 ppm of lasalocid;
from about 25 to about 100 ppm of salinomycin;
from about 5 to about 15 ppm of A-204;

from about 25 to about 100 ppm of Ionomycin.
from about 25 to about 100 ppm of X-206;
from about 50 to about 200 ppm of nigericin; and
from about 10 to about 50 ppm of dianemycin.
Amounts will be adjusted downward where both nicarbazin and 4,4'-dinitrocarbanilide are employed, and where more than one polyether is employed.

In a preferred embodiment of the present invention, compositions comprise a polyether antibiotic and nicarbazin or 4,4'-dinitrocarbanilide as the sole anticoccidial agents.

The combination of nicarbazin or 4,4'-dinitrocarbanilide and monensin, especially with the monensin in the commercially available form consisting of factor A and a minor amount of factor B, is another preferred embodiment of the present invention. A preferred combination contains from about 50 to about 75 ppm of monensin and from about 50 to about 75 ppm of nicarbazin or from about 50 to about 100 ppm of 4,4'-dinitrocarbanilide.

Poultry feedstuffs of all types and formulae in the poultry industry may be used in administering the combinations of the present invention. The following formulae are exemplary only.

Broiler Starter

| Ingredients | Percent |
|---|---|
| Corn, Yellow, Ground | 50.0 |
| Soybean Oil Meal, Solvent Extracted Dehulled (50%) | 30.9 |
| Animal Fat | 6.5 |
| Fish Meal with Solubles (60%) | 5.0 |
| Corn Distillers Dried Solubles | 4.0 |
| Dicalcium Phosphate, Feed Grade | 1.8 |
| Calcium Carbonate (Ground Limestone) | 0.8 |
| Vitamin Premix TK-01 (1.03) 1/ | 0.5 |
| Salt (NaCl) | 0.3 |
| Trace Mineral Premix TK-01 (1.02) 2/ | 0.1 |
| Methionine Hydroxy Analog | 0.1 |
| Total | 100.0 |

Broiler Grower

| Ingredients | Percent |
|---|---|
| Corn, Yellow, Ground | 57.7 |
| Soybean Meal, Solvent, Extracted, Dehulled (50%) | 31.7 |
| Animal Fat (Beef tallow) | 6.0 |
| Dicalcium Phosphate, Feed Grade | 2.7 |
| Calcium Carbonate (Ground Limestone) | 0.9 |
| Vitamin Premix TK-01 (1.03) 1/ | 0.5 |
| Salt (NaCl) | 0.2 |
| Methionine Hydroxy Analog | 0.2 |
| Trace Mineral Premix TK-01 (1.02) 2/ | 0.1 |
| Total | 100.0 |

Chick Starter, Light Breeds

| Ingredients | Percent |
|---|---|
| Corn, Yellow, Ground | 56.3 |
| Soybean Meal, Solvent Extracted, Dehulled (50%) | 17.9 |
| Wheat Middlings | 10.0 |
| Corn Distillers Dried Solubles | 5.0 |
| Fish Meal with Solubles | 5.0 |
| Alfalfa Meal, Dehydrated (17%) | 2.5 |
| Dicalcium Phosphate, Feed Grade | 1.3 |
| Calcium Carbonate | 0.9 |
| Vitamin Premix[1] | 0.5 |
| Salt (NaCl) | 0.3 |
| Methionine Hydroxy Analog | 0.2 |
| Trace Mineral Premix[2] | 0.1 |
| Total | 100.0 |

Pullet Grower

| Ingredients | Percent |
|---|---|
| Corn, Yellow, Ground | 73.5 |
| Soybean Meal, Solvent Extracted, Dehulled (50%) | 21.9 |
| Dicalcium Phosphate, Feed Grade | 2.5 |
| Calcium Carbonate | 1.0 |
| Vitamin Premix[1] | 0.5 |
| Salt (NaCl) | 0.3 |
| Methionine Hydroxy Analog | 0.2 |
| Trace Mineral Premix[2] | 0.1 |
| Total | 100.0 |

Pullet Developer

| Ingredients | Percent |
|---|---|
| Corn, Yellow, Ground | 67.5 |
| Oats, Ground Whole | 15.0 |
| Soybean Meal, Solvent Extracted, Dehulled (50%) | 13.4 |
| Dicalcium Phosphate, Feed Grade | 2.1 |
| Calcium Carbonate | 1.0 |
| Vitamin Premix[1] | 0.5 |
| Methionine Hydroxy Analog | 0.3 |
| Salt (NaCl) | 0.2 |
| Trace Mineral Premix[2] | 0.1 |
| Total | 100.0 |

Turkey Starter

| Ingredients | Percent |
|---|---|
| Soybean Meal, Solvent Extracted, Dehulled | 40.7 |
| Corn, Yellow, Ground | 39.7 |
| Fish Meal with Solubles | 5.0 |
| Beef Tallow | 5.0 |
| Corn Distillers Dried Solubles | 2.5 |
| Alfalfa Meal, Dehydrated (17%) | 2.5 |
| Dicalcium Phosphate, Feed Grade | 2.5 |
| Calcium Carbonate | 1.2 |
| Vitamin Premix[1] | 0.5 |
| Salt (NaCl) | 0.2 |
| Trace Mineral Premix[2] | 0.1 |
| Methionine Hydroxy Analog | 0.1 |
| Total | 100.0 |

Turkey Finisher

| Ingredients | Percent |
|---|---|
| Corn, Yellow, Ground | 71.2 |
| Soybean Meal, Solvent Extracted, Dehulled (50%) | 9.9 |
| Corn Distillers Dried Solubles | 5.0 |
| Alfalfa Meal, Dehydrated (17%) | 5.0 |
| Animal Fat | 3.0 |
| Fish Meal With Solubles | 2.5 |
| Dicalcium Phosphate, Feed Grade | 1.7 |
| Calcium Carbonate | 0.5 |
| Vitamin Premix[1] | 0.5 |
| Salt (NaCl) | 0.4 |
| Methionine Hydroxy Analog | 0.2 |
| Trace Mineral Premix[2] | 0.1 |

-continued

Turkey Finisher

| Ingredients | Percent |
|---|---|
| Total | 100.0 |

[1] Vitamin premix provides 3000 IU of vitamin A, 900 ICU of vitamin D, 40 mg. of vitamin E, 0.7 mg. of vitamin K, 1000 mg. of choline, 70 mg. of niacin, 4 mg. of pantothenic acid, 4 mg. of riboflavin, 0.10 mg. of vitamin $B_{12}$, 0.10 mg. of biotin and 125 mg. of ethoxyquin per kg. of complete feed.
[2] Trace mineral premix provides 75 mg. of manganese, 50 mg. of zinc, 25 mg. of iron and 1 mg. of iodine per kg. of complete feed.

The present invention was evaluated in chickens and turkeys.

The evaluations in chickens were conducted as follows: one-week-old broiler chicks were alloted to five-bird cages and were fed a medicated or control ration, typically for one day, prior to infection with oocysts of a coccidiosis-causing organism. The chicks were maintained on their respective rations for a period of time, typically seven days. Generally, there were from three to six replicates per treatment. Anticoccidial efficacy was typically determined by the lesion scores, but other measures of efficacy were employed in many of the tests. In determining lesion scores, the birds were sacrificed and the severity of lesions scored on a 0–4 scale, with lesion-free birds scored as 0, extremely severe infections scored as 4, and intermediate degrees of infection scored as 1, 2, or 3. The scores of all birds which receives a given treatment were averaged.

In those evaluations where data is reported with superscript letters, data not followed by a common letter are significantly different ($P \leq 0.05$).

The results of evaluations follows.

Test 1: *Eimeria acervulina* (strain FS-254), inoculated with 200,000 oocysts.

Lesion Scores

| | ppm | 0 | monensin 100 |
|---|---|---|---|
| nicarbazin | 0 | $3.16^c$ | $1.58^b$ |
| | 125 | $1.60^b$ | $0^a$ |

Test 2: *Eimeria tenella* (FS-226), inoculated with 100,000 oocysts.

Lesion Scores

| | ppm | 0 | monensin 100 |
|---|---|---|---|
| nicarbazin | 0 | $3.16^c$ | $1.09^b$ |
| | 125 | $1.24^b$ | $0.18^a$ |

Test 3: *Eimeria acervulina* (strain FS-254), inoculated with 40,000 oocysts

Lesion Scores

| | ppm | 0 | monensin 60 | 100 |
|---|---|---|---|---|
| nicarbazin | 0 | $3.36^e$ | $0.95^c$ | $0.80^c$ |
| | 60 | $1.05^{cd}$ | $0^a$ | $0^a$ |
| | 100 | $0.50^b$ | | |

Test 4: *Eimeria acervulina* (strain FS-254), inoculated with 200,000 oocysts.

Lesion Scores

| | ppm | 0 | monensin 100 |
|---|---|---|---|
| nicarbazin | 0 | $3.45^c$ | $1.70^b$ |
| | 75 | $2.95^c$ | $0^a$ |

Test 5: *Eimeria tenella* (strain FS-257), inoculated with 100,000 oocysts

Lesion Scores

| | ppm | 0 | monensin 100 |
|---|---|---|---|
| nicarbazin | 0 | $3.46^c$ | $1.40^b$ |
| | 125 | $1.20^b$ | $0.15^a$ |

Test 6: *Eimeria acervulina* (strain FS-254), inoculated with 1,000,000 oocysts

Lesion Scores

| | ppm | 0 | monensin 60 | 100 |
|---|---|---|---|---|
| nicorbazin | 0 | $3.45^d$ | $1.85^c$ | $1.15^b$ |
| | 60 | $2.95^d$ | $0.05^a$ | $0.11^a$ |
| | 100 | $3.00^d$ | | |

Test 7: Combination of *Eimeria acervulina* and *Eimeria maxima* (culture FS-266), 500,000 oocysts.

Lesion Scores*

| | ppm | 0 | monensin 40 | 80 | 120 |
|---|---|---|---|---|---|
| nicarbazin | 0 | $5.2^c$ | $1.8^b$ | $0.5^a$ | $0.1^a$ |
| | 40 | $1.8^b$ | $0.4^a$ | $0.4^a$ | |
| | 80 | $1.1^{ab}$ | $0.3^a$ | | |

*Lesion scores were determined at three locations, anterior, mid-, and posterior portions of the small intestine, scored on 0–4 in each section and expressed as the total.

Test 8: Combination of *Eimeria acervulina* (strain FS-254), 250,000 oocysts, and *Eimeria tenella* (strain FS-257), 50,000 oocysts. One group of birds was sacrificed at 5 days; the other group was used to evaluate oocyst production and then sacrificed at 7 days.

Intestinal lesion scores at 5-days (*Eimeria acervulina*)

| | ppm | 0 | monensin 20 | 40 | 60 | 80 | 100 |
|---|---|---|---|---|---|---|---|
| nicarbazin | 0 | $3.70^f$ | | | $1.50^{cde}$ | $1.13^{bcd}$ | $1.50^{cde}$ |
| | 20 | | $1.63^{de}$ | $1.20^{bcd}$ | $1.40^{cde}$ | $0.40^a$ | |
| | 40 | | $1.00^{bc}$ | $0.70^{ab}$ | $0.60^{ab}$ | | |
| | 60 | $1.83^e$ | $1.10^{bcd}$ | $0.70^{ab}$ | $0.40^a$ | | |
| | 80 | $1.60^{cde}$ | $0.80^{ab}$ | | | | |
| | 100 | $1.50^{cde}$ | | | | | |

Cecal lesion scores at 7-days (*Eimeria tenella*)

| | ppm | 0 | monensin 20 | 40 | 60 | 80 | 100 |
|---|---|---|---|---|---|---|---|
| nicarbazin | 0 | $3.05^f$ | | | $2.90^f$ | $2.00^e$ | $1.21^{cd}$ |
| | 20 | | $2.86^f$ | $1.90^{de}$ | $1.20^{cd}$ | $0.55^{abc}$ | |
| | 40 | | $1.15^c$ | $0.92^{bc}$ | $0.75^{abc}$ | $0^a$ | |
| | 60 | $2.05^e$ | $1.00^{bc}$ | $0.65^{bc}$ | $0.30^{ab}$ | | |

-continued

Cecal lesion scores at 7-days (*Eimeria tenella*)

| ppm | 0 | monensin 20 | 40 | 60 | 80 | 100 |
|---|---|---|---|---|---|---|
| 80 | 0.75$^{abc}$ | 0.65$^{abc}$ | 0.10$^a$ | | | |
| 100 | 0.66$^{abc}$ | | | | | |

Average oocyst passage/Bird($\times 10^6$)*

| | ppm | 0 | monensim 20 | 40 | 60 | 80 | 100 |
|---|---|---|---|---|---|---|---|
| nicarbazin | 0 | 64.8 | | | 40.9 | 53.3 | 1.1 |
| | 20 | | 64.6 | 55.6 | 7.5 | 2.0 | |
| | 40 | | 17.1 | 22.9 | 8.7 | 0.7 | |
| | 60 | 66.8 | 7.3 | 4.4 | 0.9 | | |
| | 80 | 42.9 | 1.4 | 4.7 | | | |
| | 100 | 18.7 | | | | | |

*for a 48-hour period, beginning on the 5th day following inoculation and continuing through to sacrifice.

Test 9: *Eimeria acervulina* (strain FS-273) inoculated with 1,150,000 oocysts.

Lesion Scores

| | ppm | 0 | narasin 25 | 50 | 100 |
|---|---|---|---|---|---|
| nicarbazin | 0 | 3.6$^f$ | 3.3$^f$ | 2.4$^e$ | 1.6$^d$ |
| | 25 | 3.6$^f$ | 3.2$^f$ | 0.6$^b$ | |
| | 50 | 3.6$^f$ | 1.1$^c$ | 0.1$^a$ | |
| | 100 | 1.8$^d$ | | | |

Average survivor weight gain in grams

| | ppm | 0 | narasin 25 | 50 | 100 |
|---|---|---|---|---|---|
| nicarbazin | 0 | 126.7$^a$ | 159.6$^c$ | 193.3$^{de}$ | 183.4$^d$ |
| | 25 | 142.7$^b$ | 188.3$^d$ | 212.9$^{fg}$ | |
| | 50 | 159.1$^c$ | 203.7$^{ef}$ | 216.8$^{fg}$ | |
| | 100 | 188.3$^d$ | | | |

(noninfected, nonmedicated controls = 219$^g$ grams)

Average feed/gain

| | ppm | 0 | narasin 25 | 50 | 100 |
|---|---|---|---|---|---|
| nicarbazin | 0 | 2.23$^d$ | 1.96$^{bc}$ | 1.62$^a$ | 1.60$^a$ |
| | 25 | 2.04$^c$ | 1.64$^a$ | 1.49$^a$ | |
| | 50 | 1.89$^b$ | 1.50$^a$ | 1.50$^a$ | |
| | 100 | 1.61$^a$ | | | |

(noninfected nonmedicated controls = 1.49$^a$)

Comprehensive anticoccidial indices*

| | ppm | 0 | narasin 25 | 50 | 100 |
|---|---|---|---|---|---|
| nicarbazin | 0 | 1.38(0) | 1.68(22) | 2.09(52) | 2.17(58) |
| | 25 | 1.49(8) | 1.91(39) | 2.52(84) | |
| | 50 | 1.62(17) | 2.39(75) | 2.66(94) | |
| | 100 | 2.16(57) | | | |

(noninfected, nonmedicated controls = 2.47 (100))
*Index = [growth and survival ratio] - [average lesion score/X]. Where: X = 4/[.25 X ave. growth and survival ratio of noninfected nonmedicated controls]. Growth and survival ratio = [pen weight at termination/pen weight at initiation], adjusted for mortality due to causes other than coccidiosis. Average of five replicates per treatment. The number in parentheses is the percent of optimum anticoccidial activity = [index of infected medicated group - index of infected controls]/[index of noninfected nonmedicated group - index of infected controls] × 100.

Test 10: *Eimeria acervulina* (strain FS-254), inoculated with 250,000 oocysts.

Lesion Scores

| | ppm | 0 | monensin 50 | 100 |
|---|---|---|---|---|
| nicarbazin | 0 | 2.38$^e$ | 1.36$^{cd}$ | 0.73$^{abc}$ |
| | 60 | 1.80$^{de}$ | 0.44$^{ab}$ | 0.17$^a$ |
| | 120 | 1.00$^{bc}$ | | |

Average oocyst passage/Bird ($\times 10^6$)*

| | ppm | 0 | monensin 50 | 100 |
|---|---|---|---|---|
| nicarbazin | 0 | 37.4 | 14.8 | 16.0 |
| | 60 | 44.5 | 0.7 | 2.1 |
| | 120 | 44.5 | | |

*for a 24-hour period, beginning on the 5th day following inoculation and continuing through to sacrifice on the 6th day Test 11: *Eimeria tenella* (strain FS-286), inoculated with 125,000 oocysts.

Percent mortality attributable to coccidiosis

| | | 0 | monensin 25 | 50 | 100 |
|---|---|---|---|---|---|
| nincarbazin | 0 | 32$^d$ | 24$^{cd}$ | 8$^{ab}$ | 0$^a$ |
| | 25 | 16$^{bc}$ | 0$^a$ | 0$^a$ | |
| | 50 | 4$^{ab}$ | 0$^a$ | 0$^a$ | |
| | 100 | 0$^a$ | | | | noninfected nonmedicated controls = 0$^a$

Average survivor weight in grams

| | | 0 | monensin 25 | 50 | 100 |
|---|---|---|---|---|---|
| nicarbazin | 0 | 153.4$^a$ | 165.8$^{ab}$ | 198.7$^{cd}$ | 220.3$^{de}$ |
| | 25 | 185.6$^{bc}$ | 242.5$^{ef}$ | 227.9$^e$ | |
| | 50 | 224.2$^e$ | 246.4$^{ef}$ | 244.4$^{ef}$ | |
| | 100 | 237.8$^{ef}$ | | | | noninfected nonmedicated controls = 258.2$^f$

Average feed/gain

| | | 0 | monensin 25 | 50 | 100 |
|---|---|---|---|---|---|
| nicarbazin | 0 | * | 1.64$^{cd}$ | 1.68$^d$ | 1.53$^{bc}$ |
| | 25 | 1.79$^d$ | 1.41$^a$ | 1.44$^a$ | |
| | 50 | 1.50$^{abc}$ | 1.43$^a$ | 1.42$^a$ | |
| | 100 | 1.44$^{ab}$ | | | | noninfected nonmedicated controls = 1.48$^{ab}$

*no data because of mortality which occured in all replicates

Average cecal lesion score per bird

| | | 0 | monensin 25 | 50 | 100 |
|---|---|---|---|---|---|
| nicarbazin | 0 | 3.9$^e$ | 3.8$^{de}$ | 3.3$^d$ | 0.8$^{ab}$ |
| | 25 | 3.8$^{de}$ | 2.1$^c$ | 0.8$^{ab}$ | |
| | 50 | 3.3$^d$ | 0.4$^a$ | 0.3$^a$ | |
| | 100 | 1.3$^b$ | | | |

Comprehensive anticoccidial indices*

| | | 0 | monensin 25 | 50 | 100 |
|---|---|---|---|---|---|
| nicarbazin | 0 | 0.80(0) | 1.08(13) | 1.75(43) | 2.56(80) |
| | 25 | 1.34(24) | 2.54(79) | 2.69(85) | |
| | 50 | 2.07(58) | 2.88(94) | 2.93(96) | |
| | 100 | 2.70(86) | | | | noninfected nonmedicated controls = 3.01 (100)
*for method of calculation, see Test 9, above.

Test 12: *Eimeria tenella* (strain FS-226-A-204R, a strain propagated in the presence of 15 ppm A-204 for 13 generations prior to use in this experiment), inoculated with 130,000 oocysts.

Mortality attributable to coccidiosis narasin

-continued

|  |  | 0 | 25 | 50 |
|---|---|---|---|---|
|  | 0 | 13.3[b] | 6.7[a] | 6.7[a] |
| nicarbazin | 25 | 0[a] | 0[a] | 0[a] |
|  | 50 | 0[a] | 0[a] | 0[a] | noninfected medicated controls = 0[a]

Average survivor weight gain in grams

|  |  | narasin | | |
|---|---|---|---|---|
|  |  | 0 | 25 | 50 |
|  | 0 | 172.2[a] | 243.4[c] | 239.1[c] |
| nicarbazin | 25 | 198.4[b] | 238.1[c] | 234.1[c] |
|  | 50 | 231.7[c] | 238.7[c] | 244.9[c] | noninfected nonmedicated controls = 239.7[c]

Average feed/gain

|  |  | narasin | | |
|---|---|---|---|---|
|  |  | 0 | 25 | 50 |
|  | 0 | 1.88[b] | 1.51[a] | 1.48[a] |
| nicarbazin | 25 | 1.75[b] | 1.57[a] | 1.51[a] |
|  | 50 | 1.57[a] | 1.56[a] | 1.49[a] | noninfected nonmedicated controls = 1.58[a]

Average cecal lesion per bird

|  |  | narasin | | |
|---|---|---|---|---|
|  |  | 0 | 25 | 50 |
|  | 0 | 3.8[d] | 2.7[c] | 1.5[b] |
| nicarbazin | 25 | 3.5[d] | 0.6[a] | 0.2[a] |
|  | 50 | 2.5[c] | 0.3[a] | 0[a] |

Comprehensive anticoccidial indices*

|  |  | narasin | | |
|---|---|---|---|---|
|  |  | 0 | 25 | 50 |
|  | 0 | 1.36(0) | 2.24(55) | 2.40(65) |
| nicarbazin | 25 | 1.92(35) | 2.85(93) | 2.80(90) |
|  | 50 | 2.43(67) | 2.86(94) | 2.92(98) | noninfected nonmedicated controls = 2.96 (100)

*for method of calculation, see Test 9, above.

Test 13: *Eimeria acervulina* (strain FS-254), inoculated with 1,000,000 oocysts.

Average survivor weight gain in grams

|  |  | narasin | | |
|---|---|---|---|---|
|  |  | 0 | 25 | 50 |
|  | 0 | 147.3[a] | 186.7[c] | 199.0[cd] |
| nicarbazin | 25 | 157.3[ab] | 196.9[cd] | 205.5[de] |
|  | 50 | 162.6[b] | 215.9[e] | 200.7[d] | noninfected nonmedicated controls = 217.1[e]

Average feed/gain

|  |  | narasin | | |
|---|---|---|---|---|
|  |  | 0 | 25 | 50 |
|  | 0 | 2.09[c] | 1.82[b] | 1.62[a] |
| nicarbazin | 25 | 1.81[b] | 1.57[a] | 1.51[a] |
|  | 50 | 1.96[bc] | 1.54[a] | 1.53[a] | noninfected nonmedicated controls = 1.59[a]

Average intestinal lesion score per bird

|  |  | narasin | | |
|---|---|---|---|---|
|  |  | 0 | 25 | 50 |
|  | 0 | 3.4[d] | 2.6[c] | 2.1[c] |
| nicarbazin | 25 | 3.6[d] | 1.4[b] | 0.3[a] |
|  | 50 | 3.3[d] | 0.6[a] | 0.1[a] |

Comprehensive anticoccidial indices*

|  |  | narasin | | |
|---|---|---|---|---|
|  |  | 0 | 25 | 50 |
|  | 0 | 1.58 (0) | 2.02(38) | 2.23(57) |
| nicarbazin | 25 | 1.61(3) | 2.36(68) | 2.62(91) |
|  | 50 | 1.76(16) | 2.59(88) | 2.60(89) | noninfected nonmedicated controls = 2.73 (100)

*for method of calculation, see Test 9, above.

Test 14: *Eimeria acervulina* (strain FS-273), inoculated with 780,000 oocysts.

Average survivor weight gain in grams

|  |  | salinomycin | | |
|---|---|---|---|---|
|  |  | 0 | 25 | 50 |
|  | 0 | 155.3[a] | 170.2[ab] | 199.7[cd] |
| nicarbazin | 25 | 164.5[ab] | 210.1[de] | 204.3[de] |
|  | 50 | 180.0[bc] | 209.7[de] | 209.6[de] | noninfected nonmedicated controls = 226.8[e]

Average feed/gain

|  |  | salinomycin | | |
|---|---|---|---|---|
|  |  | 0 | 25 | 50 |
|  | 0 | 1.80[d] | 1.72[bcd] | 1.63[abcd] |
| nicarbazin | 25 | 1.78[cd] | 1.56[abcd] | 1.50[ab] |
|  | 50 | 1.68[abcd] | 1.53[abc] | 1.43[a] | noninfected nonmedicated controls = 1.42[a]

Average intestinal lesion score per bird

|  |  | salinomycin | | |
|---|---|---|---|---|
|  |  | 0 | 25 | 50 |
|  | 0 | 3.9[d] | 3.7[d] | 2.9[bc] |
| nicarbazin | 25 | 3.9[d] | 2.1[b] | 0.2[a] |
|  | 50 | 3.7[cd] | 0.1[a] | 0[a] |

Comprehensive anticoccidial indices*

|  |  | salinomycin | | |
|---|---|---|---|---|
|  |  | 0 | 25 | 50 |
|  | 0 | 1.54(0) | 1.70(15) | 2.04(45) |
| nicarbazin | 25 | 1.60 (6) | 2.23 (61) | 2.54 (89) |
|  | 50 | 1.77 (21) | 2.57 (91) | 2.60 (94) | noninfected nonmedicated controls = 2.67 (100)

*for method of calculation, see Test 9, above.

Test 15: *Eimeria acervulina* (strain FS-273), inoculated with 780,000 oocysts.

Average survivor weight gain in grams

|  |  | Ionomycin | | |
|---|---|---|---|---|
|  |  | 0 | 25 | 50 |
|  | 0 | 145.7[a] | 162.4[abc] | 179.5[cde] |
| nicarbazin | 25 | 154.0[ab] | 184.3[de] | 198.6[ef] |
|  | 50 | 171.8[bcd] | 195.9[ef] | 212.7[f] | noninfected nonmedicated controls = 210.9[f]

Average feed/gain

|  |  | Ionomycin | | |
|---|---|---|---|---|
|  |  | 0 | 25 | 50 |
|  | 0 | 1.89[d] | 1.68[bc] | 1.57[ab] |
| nicarbazin | 25 | 1.80[cd] | 1.55[ab] | 1.49[a] |
|  | 50 | 1.68[bc] | 1.46[a] | 1.46[a] | noninfected nonmedicated controls = 1.43[a]

Average intestinal lesion score per bird

|  |  | Ionomycin | | |
|---|---|---|---|---|
|  |  | 0 | 25 | 50 |
|  | 0 | 3.3[d] | 3.1[d] | 1.9[c] |
| nicarbazin | 25 | 2.8[d] | 2.1[c] | 0.7[b] |
|  | 50 | 2.3[c] | 0.5[b] | 0[a] | noninfected nonmedicated controls = 0

Comprehensive anticoccidial indices*

|  |  | Ionomycin | | |
|---|---|---|---|---|
|  |  | 0 | 25 | 50 |
|  | 0 | 1.61(0) | 1.77(16) | 2.12(48) |
| nicarbazin | 25 | 1.76(15) | 2.14(50) | 2.48(83) |
|  | 50 | 1.97(35) | 2.49(83) | 2.62(96) | noninfected nonmedicated controls = 2.66 (100)

*for method of calculation, see Test 9, above.

Test 16: *Eimeria tenella* (strain FS-226-A204R), inoculated with 130,00 oocysts.

| Mortality attributable to coccidiosis | | | |
|---|---|---|---|
| | | A-204 | |
| | 0 | 5 | 10 |
| | 0 | 13.3$^b$ | 6.7$^a$ | 0$^a$ |
| nicarbazin | 50 | 0$^a$ | 0$^a$ | 0$^a$ |
| | 100 | 0$^a$ | 0$^a$ | 0$^a$ |
| noninfected nonmedicated controls = 0$^a$ | | | | |

| Average survivor weight gain in grams | | | |
|---|---|---|---|
| | | A-204 | |
| | 0 | 5 | 10 |
| | 0 | 200.9$^{ab}$ | 190.2$^a$ | 225.7$^{bc}$ |
| nicarbazin | 50 | 235.5$^c$ | 243.4$^c$ | 241.6$^c$ |
| | 100 | 232.8$^c$ | 227.2$^{bc}$ | 236.2$^c$ |
| noninfected nonmediated controls = 256.3$^c$ | | | | |

| Average feed/gain | | | |
|---|---|---|---|
| | | A-204 | |
| | 0 | 5 | 10 |
| | 0 | 1.75$^c$ | 1.74$^{bc}$ | 1.63$^{abc}$ |
| nicarbazin | 50 | 1.50$^a$ | 1.49$^a$ | 1.48$^a$ |
| | 100 | 1.54$^{ab}$ | 1.67$^{abc}$ | 1.51$^a$ |
| noninfected nonmedicated controls = 1.48$^a$ | | | | |

| Average cecal lesion score per bird | | | |
|---|---|---|---|
| | | A-204 | |
| | 0 | 5 | 10 |
| | 0 | 3.8$^e$ | 3.1$^e$ | 2.3$^d$ |
| nicarbazin | 50 | 1.9$^d$ | 0.5$^{bc}$ | 0$^a$ |
| | 100 | 0.8$^c$ | 0.1$^{ab}$ | 0$^a$ |

Comprehensive anticoccidial indices*

| | | A-204 | |
|---|---|---|---|
| | 0 | 5 | 10 |
| | 0 | 1.42(0) | 1.71(20) | 2.25(57) |
| nicarbazin | 50 | 2.42(70) | 2.70(90) | 2.79(96) |
| | 100 | 2.53(78) | 2.65(86) | 2.72(91) |
| noninfected nonmedicated controls = 2.85 (100) | | | | |

*for method of calculation, see Test 9, above.

Test 17: *Eimeria meleagrimitis* (strain FS-230-MR, pass #7)

| Mortality attributable to coccidiosis* | | | | | | | |
|---|---|---|---|---|---|---|---|
| | | | | monensin | | | |
| | | 0 | 40 | 60 | 80 | 100 | 120 |
| | 0 | 6.2 | | 6.2 | 0 | 0 | 0 |
| nicarbazin | 40 | | 0 | 0 | | | |
| | 60 | 6.2 | 0 | 0 | | | |
| | 80 | 6.2 | | | | | |
| | 100 | 0 | | | | | |
| | 120 | 0 | | | | | |

-continued

| Mortality attributable to coccidiosis* | | | | | | | |
|---|---|---|---|---|---|---|---|
| | | | | monensin | | | |
| | | 0 | 40 | 60 | 80 | 100 | 120 |
| noninfected nonmedicated controls = 0 | | | | | | | |

*There were no significant differences among treatments P≦.05.

| Average survivor weight gain in grams | | | | | | | |
|---|---|---|---|---|---|---|---|
| | | | | monensin | | | |
| | | 0 | 40 | 60 | 80 | 100 | 120 |
| ni- | 0 | 100.7$^{ab}$ | | 118.8$^{bcd}$ | 124.8$^{cd}$ | 134.1$^{de}$ | 140.3$^{de}$ |
| | 40 | | 135.8$^{de}$ | 164.6$^f$ | | | |
| car- | 60 | 98.8$^{ab}$ | 150.4$^{ef}$ | 169.3$^f$ | | | |
| | 80 | 95.7$^a$ | | | | | |
| bazin | 100 | 99.2$^{ab}$ | | | | | |
| | 120 | 112.4$^{abc}$ | | | | | |
| noninfected nonmedicated controls = 221.6$^g$ | | | | | | | |

| Average feed/gain | | | | | | | |
|---|---|---|---|---|---|---|---|
| | | | | monensin | | | |
| | | 0 | 40 | 60 | 80 | 100 | 120 |
| ni- | 0 | 2.42$^{gh}$ | | 2.17$^{def}$ | 2.16$^{def}$ | 2.07$^{de}$ | 2.00$^{bcd}$ |
| | 40 | | 2.04$^{cde}$ | 1.80$^{bc}$ | | | |
| car- | 60 | 2.63$^h$ | 1.90$^{bcd}$ | 1.77$^b$ | | | |
| | 80 | 2.55$^{gh}$ | | | | | |
| bazin | 100 | 2.53$^{gh}$ | | | | | |
| | 120 | 2.29$^{efg}$ | | | | | |
| noninfected nonmedicated controls = 1.46$^a$ | | | | | | | |

| Growth and survival ratios* | | | | | | | |
|---|---|---|---|---|---|---|---|
| | | | | monensin | | | |
| | | 0 | 40 | 60 | 80 | 100 | 120 |
| | 0 | 1.35(0) | | 1.42(11) | 1.53(30) | 1.59(39) | 1.61(44) |
| nicarbazin | 40 | | 1.59(40) | 1.71(59) | | | |
| | 60 | 1.34(0) | 1.64(48) | 1.71(60) | | | |
| | 80 | 1.33(0) | | | | | |
| | 100 | 1.42(12) | | | | | | noninfected nonmedicated controls = 1.95 (100)

*Growth and survival ratio (GSR) = pen weight at termination/pen weight at initiation, adjusted for mortality due to causes other than coccidiosis.
Data expressed as the average of four replicates/treatment.
Numbers in parentheses are the % of optimum anticoccidial activity = [GSR of infected medicated group - GSR of infected controls] / [GSR of noninfected nonmedicated group - GSR of infected controls] × 100.

The following additional tests were conducted in chickens, as described above.

Test 18: *Eimeria acervulina* (strain FS-254), inoculated with 1,000,000 oocysts.

| Lesion scores | | | | | |
|---|---|---|---|---|---|
| | | | lasalocid | | |
| | ppm | 0 | 25 | 50 | 100 |
| | 0 | 2.7$^{ef}$ | 2.4$^{cdef}$ | 2.7$^{def}$ | 1.6$^{bc}$ |
| nicarbazin | 25 | 2.8$^f$ | 2.3$^{bcdef}$ | 1.0$^{ab}$ | |
| | 50 | 2.0$^{bcde}$ | 1.7$^{bcd}$ | 0.1$^{ab}$ | |
| | 100 | 2.0$^{bcde}$ | | | |

| Average oocyst passage/Bird (×10$^6$)* | | | | | |
|---|---|---|---|---|---|
| | | | lasalocid | | |
| | ppm | 0 | 25 | 50 | 100 |
| | 0 | 51$^{ab}$ | 92$^{ab}$ | 93$^{ab}$ | 112$^{ab}$ |
| nicarbazin | 25 | 152$^b$ | 10$^{ab}$ | 12$^{ab}$ | |
| | 50 | 83$^{ab}$ | 15$^{ab}$ | 5$^a$ | |

-continued

| | 100 | $44^{ab}$ |
|---|---|---|

*for a 24-hour period, 120-144 hours post inoculation.

Test 19: *Eimeria tenella* (strain FS-257), inoculated with 200,000 oocysts.

| | | Lesion scores | | | |
|---|---|---|---|---|---|
| | | | lasalocid | | |
| | ppm | 0 | 25 | 50 | 100 |
| | 0 | $4.0^c$ | $4.0^c$ | $3.9^c$ | $3.6^c$ |
| nicarbazin | 25 | $3.9^c$ | $3.4^c$ | $2.5^b$ | |
| | 50 | $3.6^c$ | $1.9^{ab}$ | $1.6^a$ | |
| | 100 | $2.0^{ab}$ | | | |

| | | Average oocyst passage/Bird ($\times 10^6$)* | | | |
|---|---|---|---|---|---|
| | | | lasalocid | | |
| | ppm | 0 | 25 | 50 | 100 |
| | 0 | $25^{ab}$ | $51^c$ | $49^c$ | $20^{ab}$ |
| nicarbazin | 25 | $31^b$ | $13^{ab}$ | $<1^a$ | |
| | 50 | $5^a$ | $0^a$ | $0^a$ | |
| | 100 | $0^a$ | | | |

*for a 24-hour period, 144-168 hours postinoculation

Test 20: Combination of *Eimeria acervulina* (strain FS-254), 300,000 oocysts, and *Eimeria tenella* (strain FS-287), 88,000 occysts.

| | | Lesion Scores | | | |
|---|---|---|---|---|---|
| | | Intestinal | | Cecal | |
| | | (*Eimeria acervulina*)/(*Eimeria tenella*) | | | |
| | | | monensin | | |
| | ppm | 0 | 25 | 50 | 100 |
| 4,4'-di- | 0 | $2.1^{fg}/3.9^g$ | $1.9^{efg}/3.9^g$ | $1.7^{efg}/2.7^{efg}$ | $0.7^{abcd}/1.7^{bcde}$ |
| nitro- | | | | | |
| carban- | 50 | | | $0^a/0.1^a$ | |
| ilide | 100 | $0.3^{ab}/1.1^{abcd}$ | | | |

Test 21: *Eimeria tenella* (strain FS-283), 125,000 oocysts.

| | | Lesion Scores | | | |
|---|---|---|---|---|---|
| | | | monesin | | |
| | ppm | 25 | 50 | | 100 |
| | 0 | $2.8^{fg}$ | $2.1^{cdefg}$ | | $0.7^{ab}$ |
| 4,4'-dinitro- | 50 | | $1.1^{abcd}$ | | |
| carbanilide | 100 | $2.4^{defg}$ | | | |

Test 22: Combination of *Eimeria acervulina* (strain FS-280), 430,000 oocysts, and *Eimeria tenella* (strain FS-260), 43,000 oocysts.

| | | Lesion Scores | | | | | |
|---|---|---|---|---|---|---|---|
| | | Intestinal | | | | Cecal | |
| | | (*Eimeria acervulina*)/(*Eimeria tenella*) | | | | | |
| | | | | monensin | | | |
| | ppm | 0 | 25 | 50 | 75 | 100 | 125 |
| | 0 | $2.6^d/4.0^f$ | $2.3^d/3.9^f$ | $1.5^c/2.5^e$ | $0.7^b/1.2^{cd}$ | $0.2^a/0.4^{ab}$ | $0.3^a/0.7^{abc}$ |
| 4,4'-dinitro | 25 | $2.6^d/3.9^f$ | $0.8^b 2.2^e$ | $0.2^a/0.3^a$ | $0^a 0^a$ | $0^a/0^a$ | |
| carbanilide | 50 | $0.9^b/3.6^f$ | $0^a/0.2^a$ | $0^a/0^a$ | $0^a/0^a$ | | |
| | 75 | $0.2^a/2.3^e$ | $0^a/0^a$ | $0^a/0^a$ | | | |
| | 100 | $0^a 1.6^d$ | $0^a/0.1^a$ | | | | |
| | 125 | $0^a 1.0^{bcd}$ | | | | | |

We claim:

1. A process for controlling coccidiosis in poultry which comprises orally administering to the poultry a feedstuff comprising a first component which is a polyether antibiotic and a second component which is selected from the group consisting of nicarbazin and 4,4'-dinitrocarbanilide, said components being present in the feedstuff in amounts which, in combination, are synergistic as to at least one coccidiosis-causing strain of Eimeria.

2. The process of claim 1 wherein the polyether antibiotic is selected from the group consisting of monensin, narasin, lasalocid, salinomycin, A-204, lonomycin, X-206, nigericin, and dianemycin.

3. The process of claim 2 wherein the polyether antibiotic is monensin.

4. The process of claim 3 wherein the second component is nicarbazin.

5. The process of claim 4 wherein the nicarbazin is present in a concentration of from about 20 to about 125 ppm and the monensin is present in a concentration of from about 20 to about 120 ppm.

6. The process of claim 5 wherein the nicarbazin is present in a concentration of from about 50 to about 75 ppm and the monensin is present in a concentration of from about 50 to about 75 ppm.

7. The process of claim 3 wherein the second component is 4,4'-dinitrocarbanilide.

8. The process of claim 7 wherein the 4,4'-dinitrocarbanilide is present in a concentration of from about 25 to about 150 ppm and the monensin is present in a concentration of from about 20 to about 120 ppm.

9. The process of claim 8 wherein the 4,4'-dinitrocarbanilide is present in a concentration of from about 50 to about 100 ppm and the monensin is present in a concentration of from about 50 to about 75 ppm.

10. The process of claim 2 wherein the polyether antibiotic is narasin.

11. The process of claim 2 wherein the polyether antibiotic is lasalocid.

12. The process of claim 2 wherein the polyether antibiotic is salinomycin.

13. The process of claim 2 wherein the polyether antibiotic is A-204.

14. The process of claim 2 wherein the polyether antibiotic is lonomycin.

15. The process of claim 2 wherein the polyether antibiotic is X-206.

16. The process of claim 2 wherein the polyether antibiotic is nigericin.

17. The process of claim 2 wherein the polyether antibiotic is dianemycin.

18. A poultry feedstuff composition comprising a first component which is a polyether antibiotic and a second component which is selected from the group consisting of nicarbazin and 4,4'-dinitrocarbanilide, said components being present in amounts which, in combination, are synergistic as to at least one coccidiosis-causing strain of Eimeria.

19. The composition of claim 18 wherein the polyether antibiotic is monensin.

20. The composition of claim 19 wherein the second component is nicarbazin.

21. The composition of claim 20 wherein the nicarbazin is present in a concentration of from about 20 to about 125 ppm, and the monensin is present in a concentration of from about 20 to about 120 ppm.

22. The composition of claim 21 wherein the nicarbazin is present in a concentration of from about 50 to about 75 ppm, and the monensin is present in a concentration of from about 50 to about 75 ppm.

23. The composition of claim 18 wherein the second component is 4,4'-dinitrocarbanilide.

24. The composition of claim 23 wherein the 4,4'-dinitrocarbanilide is present in a concentration of from about 25 to about 150 ppm and the monensin is present in a concentration of from about 20 to about 120 ppm.

25. The composition of claim 24 wherein the 4,4'-dinitrocarbanilide is present in a concentration of from about 50 to about 100 ppm and the monensin is present in a concentration of from about 50 to about 75 ppm.

26. The composition of claim 18 wherein the polyether antibiotic is narasin.

27. The composition of claim 18 wherein the polyether antibiotic is lasalocid.

28. The composition of claim 18 wherein the polyether antibiotic is salinomycin.

29. The composition of claim 18 wherein the polyether antibiotic is A-204.

30. The composition of claim 18 wherein the polyether antibiotic is lonomycin.

31. The composition of claim 18 wherein the polyether antibiotic is X-206.

32. The composition of claim 18 wherein the polyether antibiotic is nigericin.

33. The composition of claim 18 wherein the polyether antibiotic is dianemycin.

* * * * *

REEXAMINATION CERTIFICATE (150th)

United States Patent [19]

Callender et al.

[11] B1 4,218,438

[45] Certificate Issued  Dec. 13, 1983

[54] ANTICOCCIDIAL COMBINATIONS COMPRISING NICARBAZIN AND THE POLYETHER ANTIBIOTICS

[75] Inventors: Maurice E. Callender, Indianapolis; Thomas K. Jeffers, Greenfield, both of Ind.

[73] Assignee: Eli Lilly and Company, Indianapolis, Ind.

Reexamination Request:
No. 90/000,258, Sep. 17, 1982

Reexamination Certificate for:
Patent No.: 4,218,438
Issued: Aug. 19, 1980
Appl. No.: 12,165
Filed: Feb. 14, 1979

[51] Int. Cl.$^3$ .................. A61K 31/505; A61K 31/34
[52] U.S. Cl. ...................................... 424/251; 424/285
[58] Field of Search ................................ 424/285, 251

[56] References Cited

U.S. PATENT DOCUMENTS

| | | | |
|---|---|---|---|
| 3,555,150 | 1/1971 | Gorman et al. | 424/122 |
| 3,577,531 | 5/1971 | Gorman et al. | 424/122 |
| 3,627,883 | 12/1971 | Gorman et al. | 424/122 |
| 3,839,559 | 10/1974 | Hamill et al. | 424/121 |
| 3,864,479 | 2/1975 | Miller et al. | 424/185 |

FOREIGN PATENT DOCUMENTS

1558257  1/1969  France .
1463519  2/1977  United Kingdom .

OTHER PUBLICATIONS

Abstract 1243601 from Commonwealth Agricultural Bureau Database, abstracting Coccidiosis control with anticoccidials in fattening chickens; Proc. 7th Sci. Conf. "Vet. Med. & Biotech", Zagreb, May 31–Jun. 1, 1979.

*Primary Examiner*—Sam Rosen
*Attorney, Agent, or Firm*—Kathleen R. S. Page; Leroy Whitaker; Arthur R. Whale

[57] ABSTRACT

The present invention is directed to novel anticoccidial compositions and methods of employing the same to control coccidiosis in poultry. These compositions comprise a polyether antibiotic and a second component selected from nicarbazin and 4,4'-dinitrocarbanilide.

REEXAMINATION CERTIFICATE ISSUED UNDER 35 U.S.C. 307.

ANTICOCCIDIAL COMBINATIONS COMPRISING NICARBAZIN AND THE POLYETHER ANTIBIOTICS

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, lines 29–34:
U.S. Pat. No. 3,761,594 describes the combination of meticlorpindol with 4-hydroxyquinolines. Nicarbazin has been combined with certain [quanidine] *guanidine* compounds (German Pat. No. 2,154,049). U.K. No. 1,463,519 describes the combination of purines with inter alia, monensin and nicarbazin.

Column 6, lines 19–27:
Test 6: Eimeria acervulina (strain FS-254), inoculated with 1,000,000 oocysts

| Lesion Scores | | | | |
|---|---|---|---|---|
| | | | monensin | |
| ppm | 0 | 60 | | 100 |
| [nicorbazin] *nicarbazin* 0 | $3.45^d$ | $1.85^c$ | | $1.15^b$ |
| 60 | $2.95^d$ | $[0.05^a]$ $0.50^a$ | | $0.11^a$ |
| 100 | $3.00^d$ | | | |

Column 8, lines 18–28:
Test 11: Eimeria tenella (strain FS-286), inoculated with 125,000 oocysts.

| Percent mortality attributable to coccidiosis | | | | |
|---|---|---|---|---|
| | | | monensin | |
| | 0 | 25 | 50 | 100 |
| [nincarbazin] *nicarbazin* 0 | $32^d$ | $24^{cd}$ | $8^{ab}$ | $0^a$ |
| 25 | $16^{bc}$ | $0^a$ | $0^a$ | |
| 50 | $4^{ab}$ | $0^a$ | $0^a$ | |
| 100 | $0^a$ | | | |
| noninfected nonmedicated controls = $0^a$ | | | | |

Column 11, lines 49–69:

| | | A-204 | | |
|---|---|---|---|---|
| | | 0 | 5 | 10 |
| nicarbazin | 0 | 1.42(0) | 1.71(20) | 2.25(57) |
| | 50 | 2.42(70) | 2.70(90) | 2.79(96) |
| | 100 | 2.53(78) | 2.65(86) | 2.72(91) |
| noninfected nonmedicated controls = 2.85 (100) | | | | |

*for method of calculation, see Test 9, above

*The following test was conducted in two-week-old straight run turkeys.*
Test 17: Eimeria meleagrimitis (strain FS-230-MR, pass #7)

| | Mortality attributable to coccidiosis* | | | | | |
|---|---|---|---|---|---|---|
| | | | monensin | | | |
| | 0 | 40 | 60 | 80 | 100 | 120 |
| nicarbazin 0 | 6.2 | | 6.2 | 0 | 0 | 0 |
| 40 | | 0 | 0 | | | |
| 60 | 6.2 | 0 | 0 | | | |
| 80 | 6.2 | | | | | |
| 100 | 0 | | | | | |
| 120 | 0 | | | | | |

Column 12, lines 1–8:

| Mortality attributable to coccidiosis* | | | | | | |
|---|---|---|---|---|---|---|
| | | | monensin | | | |
| | 0 | 40 | 60 | 80 | 100 | 120 |
| noninfected nonmedicated controls = 0 | | | | | | |

*There were no significant differences among treatments [$P \leq .05$] *$P \leq .05$*

Column 12, lines 32–44:

| | Growth and survival ratios* | | | | | |
|---|---|---|---|---|---|---|
| | | | monensin | | | |
| | 0 | 40 | 60 | 80 | 100 | 120 |
| nicarbazin 0 | 1.35(0) | | 1.42(11) | 1.53(30) | 1.59(39) | 1.61(44) |
| 40 | | 1.59(40) | 1.71(59) | | | |
| 60 | 1.34(0) | 1.64(48) | 1.71(60) | | | |
| 80 | 1.33(0) | | | | | |
| 100 | 1.42 (12) | | | | | |
| *120* | *1.48(22)* | | | | | |

AS A RESULT OF REEXAMINATION, IT HAS BEEN DETERMINED THAT:

Claims 15–17 and 31–33, having been finally determined to be unpatentable, are cancelled.

Claims 1, 2, and 18 are determined to be patentable as amended:

Claims 3–14 and 19–30, dependent on amended claims, are determined to be patentable.

New claims 34–41 are added and determined to be patentable.

1. A process for controlling coccidiosis in poultry which comprises orally administering to the poultry a feedstuff comprising a first component which is a polyether antibiotic *selected from the group consisting of mo-* nensin, laidlomycin, grisorixin, lenoremycin, salinomycin, narasin, lonomycin, alborixin, antibiotic 204A, etheromycin, lasalocid, isolasalocid A, lysocellin, and antibiotic A23187, and a second component which is selected from the group consisting of nicarbazin and 4,4'-dinitrocarbanilide, said components being present in the feedstuff in amounts which, in combination, are synergistic as to at least one coccidiosis-causing strain of Eimeria.

2. The process of claim 1 wherein the polyether antibiotic is selected from the group consisting of monensin, narasin, lasalocid, salinomycin, A-204 *and* lonomycin [, X206, nigericin, and dianemycin].

18. A poultry feedstuff composition comprising a first component which is a polyether antibiotic *selected from the group consisting of monensin, laidlomycin, grisorixin, lenoremycin, salinomycin, narasin, lonomycin, alborixin, antibiotic 204A, etheromycin, lasalocid, isolasalocid A, lysocellin, and antibiotic A23187,* and a second component which is selected from the group consisting of nicarbazin and 4,4'-dinitrocarbanilide, said components being present in amounts which, in combination, are synergistic as to at least one coccidiosis-causing strain of Eimeria.

34. The process of claim 10 wherein the second component is nicarbazin.

35. The process of claim 34 wherein the nicarbazin is present in a concentration of from about 20 to about 125 ppm and the narasin is present in a concentration of from about 25 to about 100 ppm.

36. The process of claim 10 wherein the second component is 4,4'-dinitrocarbanilide.

37. The process of claim 36 wherein the 4,4'-dinitrocarbanilide is present in a concentration of from about 25 to about 150 ppm and the narasin is present in a concentration of from about 25 to about 100 ppm.

38. The composition of claim 26 wherein the second component is nicarbazin.

39. The composition of claim 38 wherein the nicarbazin is present in a concentration of from about 20 to about 125 ppm, and the narasin is present in a concentration of from about 25 to about 100 ppm.

40. The composition of claim 26 wherein the second component is 4,4'-dinitrocarbanilide.

41. The composition of claim 40 wherein the 4,4'-dinitrocarbanilide is present in a concentration of from about 25 to 150 ppm and the narasin is present in a concentration of from about 25 to about 100 ppm.

* * * * *